United States Patent
Goto et al.

(10) Patent No.: US 10,421,705 B2
(45) Date of Patent: Sep. 24, 2019

(54) CARBOXYLIC ACID ESTER PRODUCTION METHOD

(71) Applicant: Mitsubishi Chemical Corporation, Chiyoda-ku (JP)

(72) Inventors: Akihiro Goto, Chiyoda-ku (JP); Yoshihiro Kamon, Chiyoda-ku (JP); Hiroyuki Mori, Chiyoda-ku (JP)

(73) Assignee: Mitsubishi Chemical Corporation, Chiyoda-ku (JP)

( * ) Notice: Subject to any disclaimer, the term of this patent is extended or adjusted under 35 U.S.C. 154(b) by 79 days.

(21) Appl. No.: 15/535,725

(22) PCT Filed: Dec. 11, 2015

(86) PCT No.: PCT/JP2015/084794
§ 371 (c)(1),
(2) Date: Jun. 14, 2017

(87) PCT Pub. No.: WO2016/098699
PCT Pub. Date: Jun. 23, 2016

(65) Prior Publication Data
US 2018/0354885 A1    Dec. 13, 2018

(30) Foreign Application Priority Data

Dec. 18, 2014  (JP) ................. 2014-255665

(51) Int. Cl.
| | | |
|---|---|---|
| *C07C 67/08* | (2006.01) | |
| *B01J 23/04* | (2006.01) | |
| *B01J 27/053* | (2006.01) | |
| *B01J 27/138* | (2006.01) | |
| *B01J 27/25* | (2006.01) | |
| *C07C 69/54* | (2006.01) | |
| *B01J 21/10* | (2006.01) | |
| *B01J 27/232* | (2006.01) | |
| *B01J 31/04* | (2006.01) | |
| *B01J 31/22* | (2006.01) | |
| *C07B 61/00* | (2006.01) | |

(52) U.S. Cl.
CPC ............ *C07C 67/08* (2013.01); *B01J 21/10* (2013.01); *B01J 23/04* (2013.01); *B01J 27/053* (2013.01); *B01J 27/138* (2013.01); *B01J 27/232* (2013.01); *B01J 27/25* (2013.01); *B01J 31/04* (2013.01); *B01J 31/2208* (2013.01); *C07C 69/54* (2013.01); *B01J 2231/49* (2013.01); *B01J 2531/22* (2013.01); *C07B 61/00* (2013.01)

(58) Field of Classification Search
CPC ............ C07C 67/08; B01J 23/04; B01J 31/04
USPC ............................................... 560/104
See application file for complete search history.

(56) References Cited

U.S. PATENT DOCUMENTS 8,859,804 B2 * 10/2014 Ansai .................. C07C 67/08
560/205

FOREIGN PATENT DOCUMENTS

| JP | 50-149612 A | 11/1975 |
|---|---|---|
| JP | 7-133252 A | 5/1995 |
| JP | 2006-63035 A | 3/2006 |
| JP | 2006-335715 A | 12/2006 |
| WO | 2015/186787 A1 | 12/2015 |

OTHER PUBLICATIONS

Wikipedia, Wikipedia, Tilde, recovered from https://en.wikipedia.org/wiki/Tilde on Mar. 23, 2017, pp. 1-19. (Year: 2017).*
Bartoli et al, Synthesis, Reaction of Dicarbonates with Carboxylic Acids Catalyzed by Weak Lewis Acids: General Method for the Synthesis of Anhydrides and Esters, 2007, 22, pp. 3489-3496. (Year: 2007).*
International Search Report dated Feb. 23, 2016 in PCT/JP2015/084794 filed Dec. 11, 2015.
Goossen, L. et al., "Lewis Acids as Highly Efficient Catalysts for the Decarboxylative Esterification of Carboxylic Acids with Dialkyl Dicarbonates," Adv. Synth. Catal., vol. 345, 2003, pp. 943-947.
Bartoli, Giuseppe et al., "Reaction of Dicarbonates with Carboxylic Acids Catalyzed by Weak Lewis Acids: General Method for the Synthesis of Anhydrides and Esters," Synthesis, No. 22, 2007, pp. 3489-3496.
Held, I. et al., "Domino Catalysis in the Direct Conversion of Carboxylic Acids to Esters," Adv. Synth. Catal. vol. 350, 2008, pp. 1891-1900.

* cited by examiner

*Primary Examiner* — Deborah D Carr
(74) *Attorney, Agent, or Firm* — Oblon, McClelland, Maier & Neustadt, L.L.P.

(57) ABSTRACT

Provided is a production method whereby corresponding carboxylic acid esters can be obtained from a variety of carboxylic acids at a high yield, even under conditions using a simple reaction operation and little catalyst and even if the amount of substrate used is theoretical. A production method for carboxylic acid ester, whereby a prescribed diester dicarbonate, carboxylic acid, and alcohol are reacted in the presence of at least one type of magnesium compound and at least one type of alkali metal compound.

13 Claims, No Drawings

CARBOXYLIC ACID ESTER PRODUCTION METHOD

TECHNICAL FIELD

The present invention relates to a method for producing a carboxylic acid ester.

BACKGROUND ART

Carboxylic acid esters are broadly used as solvents as well as raw materials for fragrances, resins, coatings, adhesives and the like. In a known carboxylic acid ester production method, di-t-butyl dicarbonate, a carboxylic acid and an alcohol are reacted to produce the corresponding carboxylic acid ester.

Non-Patent Literature 1 describes a method for producing a carboxylic acid ester by reacting di-t-butyl dicarbonate, a carboxylic acid and an alcohol in the presence of magnesium chloride.

Non-Patent Literature 2 describes a method for producing a carboxylic acid ester by reacting di-t-butyl dicarbonate, a carboxylic acid and an alcohol in the presence of an amine.

PRIOR ART LITERATURE

Non-Patent Literature

Non-Patent Literature 1: Synthesis 2007, 3489
Non-Patent Literature 2: Advanced Synthesis Catalysis, 2008, 350, 1891

SUMMARY OF THE INVENTION

Problems to be Solved by the Invention

However, in the carboxylic acid ester production method described in Non-Patent Literature 1, the amount of alcohol exceeds the theoretically estimated amount, thus making the method economically unfavorable. In addition, since it is necessary to use a catalyst at 0.1 molar equivalent to the carboxylic acid, the method is inefficient. The inventors of the present invention have studied the method and found that when the catalyst amount is reduced for reacting di-t-butyl dicarbonate, a carboxylic acid and an alcohol, reaction does not progress, or even if reaction progresses, the yield of the produced carboxylic acid ester is low. Also, the inventors have found that the substrate generality is narrow since reaction is less likely to progress when phenyl (meth) acrylate is synthesized by a known method.

In the carboxylic acid ester production method described in Non-Patent Literature 2, since it is necessary to use triethyl amine as an additive at 2 molar equivalent to the carboxylic acid, the method is inefficient. In addition, to remove the triethylamine after the reaction is completed, it is necessary to prepare an organic solvent, acidic aqueous solution and basic aqueous solution, thus resulting in a large amount of waste and making the method not only less cost-effective but also environmentally problematic. In addition, the method requires adding the alcohol and di-t-butyl dicarbonate to a −20° C. reaction mixture separately prepared and then heating the mixture to room temperature. Thus, the reaction process is complicated, and reaction efficiency is low. The inventors of the present invention have studied the method and found that when di-t-butyl dicarbonate, a carboxylic acid and an alcohol are reacted by using a reduced amount of catalyst and additive, reaction does not progress, and even if reaction progresses, the yield of the produced carboxylic acid ester is low.

Accordingly, the objective of the present invention is to provide a method for producing corresponding carboxylic acid esters from various carboxylic acids at high yield under conditions such as a simplified reaction process, a smaller amount of catalyst, and a theoretically estimated amount of substrate.

Solutions to the Problems

The inventors of the present invention have intensively studied the problems of conventional technology and found that the above objective is achieved when a specific catalyst is used for the reaction. Accordingly, the present invention has been completed.

Namely, an aspect of the present invention is a method for producing a carboxylic acid ester by reacting a compound represented by formula (I) below, a carboxylic acid and an alcohol in the presence of at least one type of magnesium compound and at least one type of alkali metal compound. In formula (I), $R^1$ and $R^2$ each indicate a C1~C20 hydrocarbon group.

[chemical 1]

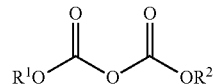

(I)

Effects of the Invention

In the carboxylic acid ester production method related to the present invention, a carboxylic acid ester is obtained at high yield even when a substrate is set at a theoretically estimated amount. Accordingly, the carboxylic acid ester is produced more efficiently and more cost-effectively than by conventional methods.

In the carboxylic acid ester production method related to the present invention, a carboxylic acid ester is obtained at high yield even when a smaller amount of catalyst is used. Accordingly, the carboxylic acid ester is produced more efficiently and more cost-effectively than by conventional methods and with less environmental load.

In the carboxylic acid ester production method related to the present invention, the raw materials are supplied into a reactor all at once. Accordingly, the carboxylic acid ester is produced more efficiently in a more simplified process than by conventional methods.

In the carboxylic acid ester production method related to the present invention, various types of carboxylic acid and various types of alcohol can be used as raw materials. Thus, the substrate generality is significantly broader than that in conventional technology.

Mode to Carry Out the Invention

In the present application, acrylic acid and methacrylic acid are collectively referred to as (meth)acrylic acid, and acrylic acid esters and methacrylic acid esters are also collectively referred to as (meth)acrylic acid esters.

[Compound Represented by Formula (I)]

In the carboxylic acid ester production method related to the present invention, a compound represented by formula (I) is used as raw material. During the reaction, a compound represented by formula (I) generates an intermediate that contains a component derived from the compound. However, the resulting carboxylic acid ester does not contain such a component that is derived from the compound.

[chemical 2]

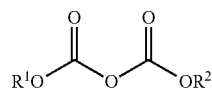

(I)

In formula (I), $R^1$ and $R^2$ each independently indicate a C1~C20 hydrocarbon group. As long as $R^1$ and $R^2$ are each a hydrocarbon group, its type and structure are not particularly limited. The hydrocarbon group may be in a linear, branched-chain or ring structure, or may have an unsaturated or ether bond. $R^1$ and $R^2$ may be bonded to form a ring structure.

Examples of a hydrocarbon group are alkyl group, alkenyl group, alkynyl group and aryl group. The number of carbon atoms in such a hydrocarbon group is preferred to be 1~20, more preferably 2~10, even more preferably 3~7, since it is easier to obtain a compound represented by formula (I) having such a group.

Particular examples of a hydrocarbon group are an allyl group, t-butyl group, t-amyl group, benzyl group and the like. Also, examples of a compound represented by formula (I) are diallyl dicarbonate, di-t-butyl dicarbonate, di-t-amyl dicarbonate, dibenzyl dicarbonate, and the like. Among them, it is preferred to be di-t-butyl dicarbonate where $R^1$ and $R^2$ are each a t-butyl group, since using such a compound makes it easier to efficiently synthesize a carboxylic acid ester.

As for a compound represented by formula (I), it is an option to use a commercially available compound or a compound produced by a known method or the like. In addition, compounds represented by formula (I) may be used alone or in combination thereof.

[Carboxylic Acid]

In the method for producing a carboxylic acid ester related to the present invention, the type and structure are not limited specifically for a carboxylic acid to be used as raw material. For example, a carboxylic acid is denoted as "$R^3$—COOH," where $R^3$ is preferred to be a C1~C30 hydrocarbon group that may have a substituent. The hydrocarbon group may be in a linear, branched-chain, or ring structure that may contain an unsaturated or ether bond. In the present application, "may have a substituent" means containing at least one substituent of any type, for example, the following bond, group or atom: ester bond, amide bond, ether bond, sulfide bond, disulfide bond, urethane bond, nitro group, cyano group, ketone group, formyl group, acetal group, thioacetal group, sulfonyl group, halogen, silicon, phosphorous and the like.

As for the hydrocarbon group in a carboxylic acid, it may be, for example, an alkyl, alkenyl, alkynyl or aryl group. The number of carbon atoms in such a hydrocarbon group is preferred to be 1~30, more preferably 2~20, considering the ease of obtaining such a carboxylic acid.

More particular examples of a hydrocarbon group are a vinyl group, isopropenyl group, t-butyl group, hexyl group, cyclohexyl group, phenyl group and the like. Specific examples of a carboxylic acid are (meth)acrylic acid, pivalic acid, heptanoic acid, cyclohexanecarboxylic acid, benzoic acid, monomethyl adipate, 6-chlorohexanoic acid, and the like. Among them, $R^3$ is more preferred to be a vinyl or isopropenyl group. It is especially preferred to use (meth)acrylic acid due to the broad application range of carboxylic acid esters.

As for a carboxylic acid, it is an option to use a commercially available type or a type produced by a known method or the like. In addition, carboxylic acids may be used alone or in combination thereof. Also, oligo- and poly-carboxylic acids may be used.

In the carboxylic acid production method related to the present invention, the amount of a carboxylic acid to be used is preferred to be in a range of 0.1~10 mol, more preferably 0.2~5 mol, even more preferably 0.5~2 mol, relative to 1 mol of the compound represented by formula (I) above. By setting the amount of a carboxylic acid to be at least 0.1 mol relative to 1 mol of the compound represented by formula (I), the yield of a resulting carboxylic acid ester is enhanced. By setting the amount of carboxylic acid to be no greater than 10 mol relative to 1 mol of the compound represented by formula (I), load on the postreaction treatment is alleviated, thus achieving more cost effective production.

[Alcohol]

In the method for producing carboxylic acid ester related to the present invention, the type and structure of an alcohol as raw material for the carboxylic acid ester are not particularly limited. For example, alcohol is denoted as "$R^4$—OH," where $R^4$ is preferred to be a C1~C30 hydrocarbon group that may have a substituent. The hydrocarbon group may be in a linear, branched-chain, or ring structure that may contain an unsaturated bond. "May have a substituent" means containing at least one substituent of any type, for example, the following bond, group or atom: ester bond, amide bond, ether bond, sulfide bond, disulfide bond, urethane bond, nitro group, cyano group, ketone group, formyl group, acetal group, thioacetal group, sulfonyl group, halogen, silicon, phosphorous and the like.

As for the hydrocarbon group contained in an alcohol, it may be, for example, an alkyl, alkenyl, alkynyl or aryl group. The number of carbon atoms in such a hydrocarbon group is preferred to be 1~30, more preferably 2~20, considering the ease of obtaining such an alcohol. Among them, the hydrocarbon group is preferred to be an aryl group. It is preferred to use aromatic alcohol capable of producing aromatic-alcohol-derived carboxylic acid esters, which conventionally have been difficult to synthesize at high yield. Specific examples are phenol, phenylphenol, naphthol, and the like.

As for an alcohol, it is an option to use a commercially available type or a type produced by a known method or the like. In addition, alcohols may be used alone or in combination thereof. Also, oligo- and poly-hydric alcohols may be used.

The amount of an alcohol to be used is preferred to be in a range of 0.1~10 mol, more preferably 0.2~5 mol, even more preferably 0.5~2 mol, relative to 1 mol of the compound represented by formula (I) above. By setting the amount of an alcohol to be at least 0.1 mol relative to 1 mol of the compound represented by formula (I), the yield of a resulting carboxylic acid ester is enhanced. By setting the amount of alcohol to be no greater than 10 mol relative to 1 mol of the compound represented by formula (I), load on the postreaction treatment is alleviated, thus making production more cost-effective.

The amount of an alcohol to be used is preferred to be in a range of 0.1~10 mol, more preferably 0.2~5 mol, even more preferably 0.5~2 mol, relative to 1 mol of the carboxylic acid. By setting the amount of an alcohol to be at least 0.1 mol relative to 1 mol of the carboxylic acid, the yield of a resulting carboxylic acid ester is enhanced. By setting the amount of alcohol to be no greater than 10 mol relative to 1 mol of the carboxylic acid, load on the postreaction treatment is alleviated, thus making production more cost-effective.

[Catalyst for Producing Carboxylic Acid Ester]

The catalyst used in the method for producing a carboxylic acid ester related to the present invention is a magnesium compound and an alkali metal compound. Since the solubility of a catalyst depends on the ligand of the catalyst, the catalyst may be used either as a homogeneous or heterogeneous catalyst.

In the method for producing a carboxylic acid ester related to the present invention, a compound represented by formula (I), a carboxylic acid and an alcohol are reacted in the presence of a catalyst. "In the presence of a catalyst" means a catalyst is present at least in part of the reaction process. It is not necessary for the catalyst to be present in the entire reaction process. In the method for producing a carboxylic acid ester related to the present invention, as long as a catalyst is added to a reaction system, the requirement of "in the presence of a catalyst" is satisfied. For example, after a catalyst is added into the reaction system, even if some change occurs in the catalyst during the reaction process, the requirement of "in the presence of a catalyst" is satisfied.

[Magnesium Compound]

Examples of a magnesium compound are salts with inorganic acids such as magnesium oxide, magnesium hydroxide, magnesium carbonate, magnesium bicarbonate, magnesium silicate, magnesium sulfate, ammonium magnesium sulfate, magnesium nitrate, magnesium phosphate, magnesium hydrogen phosphate, ammonium magnesium phosphate, magnesium borate, magnesium salts of halogen acids, magnesium perhalogenates, and magnesium salts of hydrohalic acids; salts with organic acids such as magnesium carboxylate, magnesium peroxycarboxylate, and magnesium sulfonate; complex salts such as magnesium acetylacetonate, magnesium hexafluoroacetylacetonate, magnesium porphyrin, magnesium phthalocyanine, and magnesium cyclopentadienyl. These magnesium salts are not limited to any particular type; for example, they may be any hydrate or anhydride. Among them, magnesium oxide, magnesium hydroxide, magnesium carbonate, magnesium sulfate, ammonium magnesium sulfate, magnesium nitrate, magnesium salts of hydrohalic acids, magnesium carboxylate, and magnesium complex are preferred. More specific examples of a magnesium compound are magnesium oxide, magnesium hydroxide, magnesium carbonate hydroxide (also known as basic magnesium carbonate), magnesium sulfate, ammonium magnesium sulfate, magnesium nitrate, magnesium chloride, magnesium bromide, magnesium acetate, magnesium benzoate, magnesium (meth)acrylate, magnesium acetylacetonate, and the like.

As for a magnesium compound, it is an option to use a commercially available type or a type produced by a known method or the like. In addition, such compounds may be used alone or in combination thereof.

The amount of a magnesium compound to be used is not particularly limited as long as a carboxylic acid ester is produced. The amount of a magnesium compound is preferred to be in a range of 0.001~1000 mol %, more preferably 0.005~500 mol %, relative to the compound represented by formula (I). By setting the amount of a magnesium compound to be at least 0.001 mol % of the compound represented by formula (I), the yield of a resulting carboxylic acid ester is enhanced. The amount is preferred to be no greater than 1000 mol % of the compound represented by formula (I), because any significant increase in the effect is unlikely if it is set beyond 1000 mol %.

The amount of a magnesium compound is preferred to be in a range of 0.001~1000 mol %, more preferably 0.005~500 mol %, even more preferably 0.01~250 mol %, relative to the amount of alcohol. By setting the amount of a magnesium compound to be at least 0.001 mol % of the alcohol, the yield of a resulting carboxylic acid ester is enhanced. The amount is preferred to be no greater than 1000 mol % of the alcohol, because any significant increase in the effect is unlikely if it is set beyond 1000 mol %.

[Alkali Metal Compound]

Examples of an alkali metal compound are salts with inorganic acids such as alkali metal hydrides, oxides, hydroxides, carbonates, bicarbonates, sulfates, nitrates, phosphates, borates, salts of halogen acids, perhalogenates, salts of hydrohalic acids, and thiocyanates; salts with organic acids such as alkali metal alkoxides, carboxylates, and sulfonates; salts with organic bases such as alkali metal amides and sulfoamides; complex salts such as alkali metal acetylacetonates, hexafluoroacetylacetonates, porphyrins, phthalocyanates, and cyclopentadienates. These alkali metal salts are not limited to any particular type; for example, they may be any hydrate or anhydride. Among them, alkali metal oxides, hydroxides, carbonates, dicarbonates, salts of hydrohalic acids, carboxylates, amides and complexes are preferred.

The metal in an alkali metal compound is not limited specifically. Among the metals that belong to alkali metals, lithium, sodium, potassium, rubidium and cesium are preferred, more preferably lithium, because of high catalytic activity. Specific examples of a lithium compound are lithium oxide, lithium hydroxide, lithium carbonate, lithium fluoride, lithium chloride, lithium bromide, lithium acetate, lithium benzoate, lithium (meth)acrylate, lithium amide, lithium triflimide, lithium acetylacetonate, and the like.

Alkali metal compounds may be obtained commercially, or produced by a known method or the like. They may be used alone or in combination thereof.

The amount of an alkali metal compound to be used is not particularly limited as long as a carboxylic acid ester is produced. The amount of an alkali metal compound is preferred to be in a range of 0.001~1000 mol %, more preferably 0.005~500 mol %, relative to the compound represented by formula (I). By setting the amount of an alkali metal compound to be at least 0.001 mol % of the compound represented by formula (I), the yield of a resulting carboxylic acid ester is enhanced. The amount is preferred to be no greater than 1000 mol % of the compound represented by formula (I), because any significant increase in the effect is unlikely if it is set beyond 1000 mol %.

The amount of an alkali metal compound is preferred to be in a range of 0.001~1000 mol %, more preferably 0.005~500 mol %, even more preferably 0.01~250 mol % relative to the amount of alcohol. By setting the amount of an alkali metal compound to be at least 0.001 mol % of the alcohol, the yield of a resulting carboxylic acid ester is enhanced. The amount is preferred to be no greater than 1000 mol % of the alcohol, because any significant increase in the effect is unlikely if it is set beyond 1000 mol %.

[Reaction Conditions for Producing Carboxylic Acid Ester]

The reaction conditions in the method for producing carboxylic acid ester related to the present invention are not particularly limited, and may be modified appropriately during the reaction process.

The reactor is not limited to any particular type. The reaction temperature is not limited specifically either, and may be set in a range of –20~180° C., preferably 0~100° C. By setting the reaction temperature to be at least –20° C., reaction progresses efficiently. When the reaction temperature is set at 180° C. or lower, the amount of byproduct is controlled and the coloring of the reaction mixture is suppressed.

The reaction time is not limited specifically; for example, it may be set for 0.5~72 hours, preferably 2~48 hours. When the reaction time is set to be at least 0.5 hours, reaction will progress sufficiently. The reaction time is set to be 72 hours or shorter, because any duration longer than 72 hours does not result in any significant increase in the effect.

No specific limitation is set on reaction ambience or reaction pressure.

The method for producing a carboxylic acid ester related to the present invention does not require any solvent. However, a solvent may be used depending on the situations such as when the viscosity of the reaction mixture is high. The type of solvent is not limited specifically; for example, a C1~C25 organic compound may be used by selecting appropriately according to reaction conditions. Examples of a solvent are tetrahydrofuran and the like. Solvents may be used alone or in combination thereof. The amount of solvent is not limited particularly, and may be determined appropriately.

The raw material (compound represented by formula (I), carboxylic acid and alcohol), catalyst, solvent and the like if applicable, to be used for reaction, may be introduced into a reactor by any method; for example, all of the material may be introduced all at once, or part or all of the material may be introduced intermittently or continuously. Alternatively, a combination of those methods may be employed.

[Carboxylic Acid Ester]

The product obtained by the method for producing a carboxylic acid ester related to the present invention is denoted, for example, as "$R^3COOR^4$." $R^3$ and $R^4$ are those shown above in the descriptions of carboxylic acids and alcohols.

When a carboxylic acid used in the production method related to the present invention is (meth)acrylic acid, a (meth)acrylic acid ester is produced. Since (meth)acrylic acid and (meth)acrylic acid ester tend to polymerize, a polymerization inhibitor may be added in advance so as to prevent their polymerization. A polymerization inhibitor may be added at any time, but is preferred to be added at the start of reaction, since it is easier to carry out the reaction.

The type of polymerization inhibitor is not particularly limited; for example, it may be a known polymerization inhibitor such as 2,2,6,6-tetramethylpiperidine 1-oxyl free radical or the like. The inhibitors may be used alone or in combination thereof. The amount of polymerization inhibitor is preferred to be in a range of 0.001~0.5 parts by mass, more preferably 0.01~0.1 parts by mass, relative to 100 parts by mass of (meth)acrylic acid or (meth)acrylic acid ester. In addition, reaction may be carried out in a flow of an oxygen-containing gas such as air. The flow rate of gas may be determined according to reaction conditions or the like.

The carboxylic acid ester obtained by the method for producing a carboxylic acid ester related to the present invention may be used as is for the following reaction, or purified if necessary. Conditions for purifying the ester are not limited specifically, and may be modified appropriately during the reaction process or at the time of reaction completion. For example, after the reaction is completed, a carboxylic acid ester may be purified from the reaction mixture by vacuum distillation, chromatography, recrystallization or the like. Those methods may be employed alone or in combination thereof.

In the method for producing a carboxylic acid ester related to the present invention, the storage container for the obtained carboxylic acid ester is not particularly limited; for example, a glass, resin or metallic container may be used.

EXAMPLES

In the following, the present invention is described in detail by referring to examples. However, the present invention is not limited to those examples, and any modification is possible unless it deviates from the gist of the present invention.

The di-t-butyl dicarbonate used in the examples and comparative examples below is a compound with a purity of 98 mass % made by Tokyo Chemical Industry Co., Ltd., and $R^1$ and $R^2$ in formula (I) are $C(CH_3)_3$. In addition, tetrahydrofuran (hereinafter abbreviated as "THF") is a special grade (moisture rate of 0.05% or less) made by Kanto Chemical Co., Inc. The method for determining the yield of each product is as follows.

After the reaction was completed, a standard substance (anisole or 1,1,2,2-tetrachloroethane) was added to the reaction mixture. Then, the mixture was dissolved in deuterated chloroform ($CDCl_3$) and was analyzed by $^1$H-NMR (270 MHz). By converting from the values obtained from integration of the signal intensities on the spectrum, the amount (mmol) of the produced carboxylic acid ester was determined. Next, the yield of the carboxylic acid ester was calculated by formula (1) (when the obtained yield is less than 1%, it will be denoted as zero).

$$\text{Yield of carboxylic acid ester (\%)} = (P_1/R_1) \times 100 \quad (1)$$

$P_1$=the amount of produced carboxylic acid ester (mmol)
$R_1$=the amount of alcohol used in the reaction (mmol)

Also, the amount (mol %) of each magnesium compound and alkali metal compound used as the catalyst was calculated by formula (2).

$$\text{The amount of catalyst (mol \%)} = (C_1/R_1) \times 100 \quad (2)$$

$C_1$=the amount of catalyst used in the reaction (mmol)
$R_1$=the amount of alcohol used in the reaction (mmol)

Example 1

In a 100 mL capacity eggplant-shaped flask, 10.000 grams (106.26 mmol) of phenol, 9.148 grams (106.26 mmol) of methacrylic acid, 23.664 grams (106.26 mmol) of di-t-butyl dicarbonate, 0.018 grams (0.43 mmol, 0.4 mol %) of lithium hydroxide monohydrate, and 0.024 grams (0.11 mmol, 0.1 mol %) of magnesium acetylacetonate were added successively. Then reaction was carried out at 25° C. while the mixture was stirred. Accordingly, phenyl methacrylate was produced. The reaction result obtained 5 hours after the start of reaction is shown in Table 1.

Examples 2~14

In each of the examples, phenyl methacrylate was produced by conducting the same procedure as in Example 1 except that lithium hydroxide monohydrate as the catalyst was replaced with a type of alkali metal compound (0.4 mol %) shown in Table 1. The reaction result obtained 5 hours after the start of reaction in each example is shown in Table 1.

Comparative Example 1

Phenyl methacrylate was produced by carrying out the same procedure as in Example 1 except that lithium hydroxide monohydrate was not added. The reaction result obtained 5 hours after the start of reaction is shown in Table 1.

Comparative Example 2

The comparative example was conducted in an attempt to produce phenyl methacrylate by carrying out the same procedure as in Example 1 except that magnesium acetylacetonate was not added. The reaction result obtained 5 hours after the start of reaction is shown in Table 1.

Comparative Example 3

The comparative example was conducted in an attempt to produce phenyl methacrylate by carrying out the same procedure as in Comparative Example 2 except that the amount of lithium hydroxide monohydrate was changed to 2.0 mol %. The reaction result obtained 24 hours after the start of reaction is shown in Table 1.

Comparative Examples 4~10

Each comparative example was conducted in an attempt to produce phenyl methacrylate by the same procedure as in Comparative Example 2 except that lithium hydroxide monohydrate was replaced with a type and amount of alkali metal compound (1.0 mol % or 2.0 mol %) specified in Table 1. The reaction result of each comparative example obtained 24 hours after the start of reaction is shown in Table 1.

TABLE 1

|  | magnesium compound | added amount (mol %) | alkali metal compound | added amount (mol %) | reaction time (hr.) | yield of phenyl methacrylate (%) |
| --- | --- | --- | --- | --- | --- | --- |
| Example 1 | magnesium acetylacetonate | 0.1 | lithium hydroxide monohydrate | 0.4 | 5 | 82 |
| Example 2 | magnesium acetylacetonate | 0.1 | cesium hydroxide monohydrate | 0.4 | 5 | 56 |
| Example 3 | magnesium acetylacetonate | 0.1 | lithium carbonate | 0.4 | 5 | 78 |
| Example 4 | magnesium acetylacetonate | 0.1 | sodium carbonate | 0.4 | 5 | 72 |
| Example 5 | magnesium acetylacetonate | 0.1 | potassium carbonate | 0.4 | 5 | 68 |
| Example 6 | magnesium acetylacetonate | 0.1 | rubidium carbonate | 0.4 | 5 | 53 |
| Example 7 | magnesium acetylacetonate | 0.1 | cesium carbonate | 0.4 | 5 | 42 |
| Example 8 | magnesium acetylacetonate | 0.1 | lithium oxide | 0.4 | 5 | 73 |
| Example 9 | magnesium acetylacetonate | 0.1 | lithium acetylacetonate | 0.4 | 5 | 67 |
| Example 10 | magnesium acetylacetonate | 0.1 | lithium fluoride | 0.4 | 5 | 77 |
| Example 11 | magnesium acetylacetonate | 0.1 | lithium chloride | 0.4 | 5 | 82 |
| Example 12 | magnesium acetylacetonate | 0.1 | lithium bromide | 0.4 | 5 | 86 |
| Example 13 | magnesium acetylacetonate | 0.1 | lithium amide | 0.4 | 5 | 82 |
| Example 14 | magnesium acetylacetonate | 0.1 | lithium triflimide | 0.4 | 5 | 71 |
| Comp. Example 1 | magnesium acetylacetonate | 0.1 | — | — | 5 | 19 |
| Comp. Example 2 | — | — | lithium hydroxide monohydrate | 0.4 | 5 | 0 |
| Comp. Example 3 | — | — | lithium hydroxide monohydrate | 2.0 | 24 | 0 |
| Comp. Example 4 | — | — | cesium hydroxide monohydrate | 2.0 | 24 | 0 |
| Comp. Example 5 | — | — | lithium carbonate | 2.0 | 24 | 0 |
| Comp. Example 6 | — | — | sodium carbonate | 2.0 | 24 | 0 |
| Comp. Example 7 | — | — | potassium carbonate | 2.0 | 24 | 0 |
| Comp. Example 8 | — | — | rubidium carbonate | 2.0 | 24 | 0 |
| Comp. Example 9 | — | — | cesium carbonate | 2.0 | 24 | 0 |
| Comp. Example 10 | — | — | lithium bromide | 1.0 | 24 | 0 |

Examples 15~19

In each example, phenyl methacrylate was produced by carrying out the same procedure as in Example 1 except that the amount of lithium hydroxide monohydrate (0.1 mol %~2.0 mol %) specified in Table 2 was used. The reaction result of each example obtained 5 hours or 24 hours after the start of reaction is shown in Table 2.

TABLE 2

|  | magnesium compound | added amount (mol %) | alkali metal compound | added amount (mol %) | reaction time (hr.) | yield of phenyl methacrylate (%) |
|---|---|---|---|---|---|---|
| Example 15 | magnesium acetylacetonate | 0.1 | lithium hydroxide monohydrate | 0.1 | 5<br>24 | 90<br>94 |
| Example 16 | magnesium acetylacetonate | 0.1 | lithium hydroxide monohydrate | 0.2 | 5<br>24 | 86<br>95 |
| Example 17 | magnesium acetylacetonate | 0.1 | lithium hydroxide monohydrate | 0.4 | 5<br>24 | 82<br>96 |
| Example 18 | magnesium acetylacetonate | 0.1 | lithium hydroxide monohydrate | 0.8 | 24 | 96 |
| Example 19 | magnesium acetylacetonate | 0.1 | lithium hydroxide monohydrate | 2.0 | 24 | 96 |

Examples 20~31

In each example, phenyl methacrylate was produced by carrying out the same procedure as in Example 1 except that magnesium acetylacetonate was replaced with the type and amount of magnesium compound (0.05 mol %~0.5 mol %) specified in Table 3, and the amount of lithium hydroxide monohydrate specified in Table 3 was used (0.2 mol %~2.0 mol %). The reaction result of each example obtained 5 hours or 24 hours after the start of reaction is shown in Table 3.

Comparative Examples 11~22

Each comparative example was conducted to produce, or in an attempt to produce, phenyl methacrylate by carrying out the same procedure as in Examples 20~31 except that lithium hydroxide monohydrate was not added. The reaction result of each comparative example obtained 5 hours or 24 hours after the start of reaction is shown in Table 3.

TABLE 3

|  | magnesium compound | added amount (mol %) | alkali metal compound | added amount (mol %) | reaction time (hr.) | yield of phenyl methacrylate (%) |
|---|---|---|---|---|---|---|
| Example 20 | magnesium acetate tetrahydrate | 0.05 | lithium hydroxide monohydrate | 0.2 | 24 | 93 |
| Example 21 | magnesium benzoate trihydrate | 0.05 | lithium hydroxide monohydrate | 0.2 | 24 | 93 |
| Example 22 | magnesium methacrylate | 0.05 | lithium hydroxide monohydrate | 0.2 | 24 | 93 |
| Example 23 | magnesium hydroxide | 0.1 | lithium hydroxide monohydrate | 0.4 | 5 | 81 |
| Example 24 | magnesium chloride | 0.1 | lithium hydroxide monohydrate | 0.4 | 5 | 84 |
| Example 25 | magnesium chloride hexahydrate | 0.2 | lithium hydroxide monohydrate | 0.8 | 5 | 67 |
| Example 26 | magnesium bromide hexahydrate | 0.2 | lithium hydroxide monohydrate | 0.8 | 5 | 85 |
| Example 27 | magnesium nitrate hexahydrate | 0.2 | lithium hydroxide monohydrate | 0.8 | 5 | 82 |
| Example 28 | magnesium sulfate | 0.2 | lithium hydroxide monohydrate | 0.8 | 24 | 92 |
| Example 29 | ammonium magnesium sulfate hexahydrate | 0.2 | lithium hydroxide monohydrate | 0.8 | 24 | 46 |
| Example 30 | magnesium oxide | 0.5 | lithium hydroxide monohydrate | 2.0 | 24 | 97 |
| Example 31 | magnesium carbonate hydroxide | 0.5 | lithium hydroxide monohydrate | 2.0 | 24 | 96 |

TABLE 3-continued

| | magnesium compound | added amount (mol %) | alkali metal compound | added amount (mol %) | reaction time (hr.) | yield of phenyl methacrylate (%) |
|---|---|---|---|---|---|---|
| Comp. Example 11 | magnesium acetate tetrahydrate | 0.05 | — | — | 24 | 88 |
| Comp. Example 12 | magnesium benzoate trihydrate | 0.05 | — | — | 24 | 85 |
| Comp. Example 13 | magnesium methacrylate | 0.05 | — | — | 24 | 88 |
| Comp. Example 14 | magnesium hydroxide | 0.1 | — | — | 5 | 49 |
| Comp. Example 15 | magnesium chloride | 0.1 | — | — | 5 | 0 |
| Comp. Example 16 | magnesium chloride hexahydrate | 0.2 | — | — | 5 | 1 |
| Comp. Example 17 | magnesium bromide hexahydrate | 0.2 | — | — | 5 | 1 |
| Comp. Example 18 | magnesium nitrate hexahydrate | 0.2 | — | — | 5 | 5 |
| Comp. Example 19 | magnesium sulfate | 0.2 | — | — | 24 | 0 |
| Comp. Example 20 | ammonium magnesium sulfate hexahydrate | 0.2 | — | — | 24 | 0 |
| Comp. Example 21 | magnesium oxide | 0.5 | — | — | 24 | 74 |
| Comp. Example 22 | magnesium carbonate hydroxide | 0.5 | — | — | 24 | 64 |

Example 32

In a 100 mL capacity eggplant-shaped flask, 10.000 grams (106.26 mmol) of phenol, 7.657 grams (106.26 mmol) of acrylic acid, 23.664 grams (106.26 mmol) of di-t-butyl dicarbonate, 0.046 grams (0.53 mmol, 0.5 mol %) of lithium bromide, and 0.064 grams (0.53 mmol, 0.5 mol %) of magnesium sulfate were added successively. Then, reaction was carried out at 25° C. while the mixture was stirred. Accordingly, phenyl acrylate was produced. The reaction result obtained 24 hours after the start of reaction is shown in Table 4.

Examples 33~35

Phenyl acrylate was produced in each of the examples by conducting the same procedure as in Example 32 except that lithium bromide was replaced with a type of alkali metal compound (0.5 mol %) specified in Table 4. The reaction result of each example obtained 24 hours after the start of reaction is shown in Table 4.

Comparative Example 23

The comparative example was conducted in an attempt to produce phenyl acrylate by the same procedure as in Example 32 except that lithium bromide was not added. The reaction result obtained 24 hours after the start of reaction is shown in Table 4.

Comparative Example 24

The comparative example was conducted in an attempt to produce phenyl acrylate by the same procedure as in Example 32 except that magnesium sulfate was not added. The reaction result obtained 24 hours after the start of reaction is shown in Table 4.

TABLE 4

| | magnesium compound | added amount (mol %) | alkali metal compound | added amount (mol %) | reaction time (hr.) | yield of phenyl acrylate (%) |
|---|---|---|---|---|---|---|
| Example 32 | magnesium sulfate | 0.5 | lithium bromide | 0.5 | 24 | 48 |
| Example 33 | magnesium sulfate | 0.5 | lithium acetylacetonate | 0.5 | 24 | 68 |
| Example 34 | magnesium sulfate | 0.5 | lithium carbonate | 0.5 | 24 | 77 |
| Example 35 | magnesium sulfate | 0.5 | lithium hydroxide monohydrate | 0.5 | 24 | 78 |
| Comp. Example 23 | magnesium sulfate | 0.5 | — | — | 24 | 0 |
| Comp. Example 24 | — | — | lithium bromide | 0.5 | 24 | 0 |

Example 36

In a 1 L capacity eggplant-shaped flask, 153.370 grams (1629.69 mmol) of phenol, 140.300 grams (1629.69 mmol) of methacrylic acid, 362.938 grams (1629.69 mmol) of di-t-butyl dicarbonate, 0.027 grams (0.65 mmol, 0.04 mol %) of lithium hydroxide monohydrate, and 0.010 grams (0.16 mmol, 0.01 mol %) of magnesium hydroxide were added successively. Then reaction was carried out at 25° C. while the mixture was stirred. Accordingly, phenyl methacrylate was produced. The reaction result obtained 48 hours after the start of reaction is shown in Table 5.

Examples 37~62

By using the material, catalyst and solvent shown in Tables 5~7 under the conditions specified in those tables and a smaller eggplant-shaped flask when applicable, corresponding carboxylic acid esters were produced by conducting the same procedure as in Example 36. The reaction results are shown in Tables 5~7.

TABLE 5

| | carboxylic acid (mol eq.) | added amount (mmol) | compound by formula (I) (mol eq.) | alcohol (mol eq.) | magnesium compound | added amount (mol %) | alkali metal compound |
|---|---|---|---|---|---|---|---|
| Example 36 | methacrylic acid (1.00) | 1629.69 | di-t-butyl dicarbonate (1.00) | phenol (1.00) | magnesium hydroxide | 0.01 | lithium hydroxide monohydrate |
| Example 37 | methacrylic acid (1.00) | 815.43 | di-t-butyl dicarbonate (1.00) | 2-phenylphenol (1.00) | magnesium hydroxide | 0.02 | lithium hydroxide monohydrate |
| Example 38 | methacrylic acid (1.00) | 326.40 | di-t-butyl dicarbonate (1.00) | 4-phenylphenol (1.00) | magnesium hydroxide | 0.05 | lithium hydroxide monohydrate |
| Example 39 | methacrylic acid (1.00) | 815.43 | di-t-butyl dicarbonate (1.00) | 1-naphthol (1.00) | magnesium hydroxide | 0.02 | lithium hydroxide monohydrate |
| Example 40 | methacrylic acid (1.00) | 326.40 | di-t-butyl dicarbonate (1.00) | 2-naphthol (1.00) | magnesium hydroxide | 0.05 | lithium hydroxide monohydrate |
| Example 41 | methacrylic acid (1.00) | 326.40 | di-t-butyl dicarbonate (1.00) | 2-naphthol (1.00) | magnesium hydroxide | 0.05 | lithium hydroxide monohydrate |
| Example 42 | methacrylic acid (1.00) | 1800.02 | di-t-butyl dicarbonate (1.00) | phenol (0.91) | magnesium hydroxide | 0.01 | lithium hydroxide monohydrate |
| Example 43 | methacrylic acid (1.00) | 1800.02 | di-t-butyl dicarbonate (1.00) | phenol (0.91) | magnesium hydroxide | 0.01 | lithium carbonate |

| | added amount (mol %) | solvent (mL) | reaction temp. (° C.) | reaction time (hr.) | yield of carboxylic acid ester (%) |
|---|---|---|---|---|---|
| Example 36 | 0.04 | — | 25 | 48 | 96 |
| Example 37 | 0.2 | — | 25 | 24 | 98 |
| Example 38 | 0.5 | THF (215) | 25 | 24 | 96 |
| Example 39 | 0.2 | — | 25 | 24 | 98 |
| Example 40 | 0.5 | THF (110) | 25 | 24 | 91 |
| Example 41 | 0.5 | THF (110) | 40 | 5 | 97 |
| Example 42 | 0.04 | — | 25 | 48 | 97 |
| Example 43 | 0.05 | — | 25 | 48 | 91 |

TABLE 6

| | carboxylic acid (mol eq.) | added amount (mmol) | compound by formula (I) (mol eq.) | alcohol (mol eq.) | magnesium compound | added amount (mol %) | alkali metal compound |
|---|---|---|---|---|---|---|---|
| Example 44 | acrylic acid (1.00) | 358.67 | di-t-butyl dicarbonate (1.00) | 2-phenylphenol (0.91) | magnesium hydroxide | 0.05 | lithium carbonate |
| Example 45 | acrylic acid (1.00) | 358.67 | di-t-butyl dicarbonate (1.00) | 2-phenylphenol (0.91) | magnesium hydroxide | 0.05 | lithium carbonate |
| Example 46 | acrylic acid (1.00) | 358.67 | di-t-butyl dicarbonate (1.00) | 2-phenylphenol (0.91) | magnesium hydroxide | 0.05 | lithium carbonate |

TABLE 6-continued

| | carboxylic acid | added amount | compound by formula (I) | alcohol | magnesium compound | added amount (mol %) | alkali metal compound |
|---|---|---|---|---|---|---|---|
| Example 47 | acrylic acid (1.00) | 358.67 | di-t-butyl dicarbonate (1.00) | 2-phenylphenol (0.91) | magnesium hydroxide | 0.05 | lithium carbonate |
| Example 48 | acrylic acid (1.00) | 358.67 | di-t-butyl dicarbonate (1.00) | 4-phenylphenol (0.91) | magnesium hydroxide | 0.05 | lithium carbonate |
| Example 49 | acrylic acid (1.00) | 358.60 | di-t-butyl dicarbonate (1.00) | 1-naphthol (0.91) | magnesium hydroxide | 0.05 | lithium hydroxide monohydrate |
| Example 50 | acrylic acid (1.00) | 358.60 | di-t-butyl dicarbonate (1.00) | 1-naphthol (0.91) | magnesium hydroxide | 0.05 | lithium carbonate |
| Example 51 | acrylic acid (1.00) | 358.60 | di-t-butyl dicarbonate (1.00) | 1-naphthol (0.91) | magnesium hydroxide | 0.05 | lithium carbonate |
| Example 52 | acrylic acid (1.00) | 358.60 | di-t-butyl dicarbonate (1.00) | 2-naphthol (0.91) | magnesium hydroxide | 0.05 | lithium hydroxide monohydrate |
| Example 53 | acrylic acid (1.00) | 358.60 | di-t-butyl dicarbonate (1.00) | 2-naphthol (0.91) | magnesium hydroxide | 0.05 | lithium carbonate |

| | added amount (mol %) | solvent (mL) | reaction temp. (° C.) | reaction time (hr.) | yield of carboxylic acid ester (%) |
|---|---|---|---|---|---|
| Example 44 | 0.25 | — | 25 | 24 | 82 |
| Example 45 | 0.25 | — | 50 | 6 | 92 |
| Example 46 | 0.25 | THF (30) | 25 | 24 | 98 |
| Example 47 | 0.25 | THF (30) | 50 | 6 | 98 |
| Example 48 | 0.25 | THF (30) | 25 | 24 | 97 |
| Example 49 | 0.25 | — | 25 | 24 | 94 |
| Example 50 | 0.25 | — | 25 | 24 | 94 |
| Example 51 | 0.25 | — | 50 | 6 | 95 |
| Example 52 | 0.25 | — | 25 | 24 | 92 |
| Example 53 | 0.25 | — | 25 | 24 | 95 |

TABLE 7

| | carboxylic acid (mol eq.) | added amount (mmol) | compound by formula (I) (mol eq.) | alcohol (mol eq.) | magnesium compound | added amount (mol %) | alkali metal compound |
|---|---|---|---|---|---|---|---|
| Example 54 | heptanoic acid (1.00) | 342.52 | di-t-butyl dicarbonate (1.00) | phenol (0.95) | magnesium hydroxide | 0.05 | lithium hydroxide monohydrate |
| Example 55 | cyclohexane carboxylic acid (1.00) | 342.52 | di-t-butyl dicarbonate (1.00) | phenol (0.95) | magnesium hydroxide | 0.05 | lithium hydroxide monohydrate |
| Example 56 | cyclohexane carboxylic acid (1.00) | 342.52 | di-t-butyl dicarbonate (1.00) | phenol (0.95) | magnesium hydroxide | 0.05 | lithium carbonate |
| Example 57 | pivalic acid (1.00) | 342.52 | di-t-butyl dicarbonate (1.00) | phenol (0.95) | magnesium hydroxide | 0.05 | lithium hydroxide monohydrate |
| Example 58 | benzoic acid (1.00) | 342.52 | di-t-butyl dicarbonate (1.00) | phenol (0.95) | magnesium hydroxide | 0.05 | lithium hydroxide monohydrate |
| Example 59 | benzoic acid (1.00) | 342.52 | di-t-butyl dicarbonate (1.00) | phenol (0.95) | magnesium hydroxide | 0.05 | lithium hydroxide monohydrate |
| Example 60 | adipic acid monomethyl (1.00) | 163.64 | di-t-butyl dicarbonate (1.00) | phenol (1.00) | magnesium hydroxide | 0.1 | lithium hydroxide monohydrate |
| Example 61 | adipic acid monomethyl (1.00) | 163.64 | di-t-butyl dicarbonate (1.00) | phenol (1.00) | magnesium hydroxide | 1.0 | lithium hydroxide monohydrate |
| Example 62 | 6-chlorohexanoic acid (1.00) | 23.38 | di-t-butyl dicarbonate (1.00) | phenol (1.00) | magnesium hydroxide | 1.0 | lithium hydroxide monohydrate |

TABLE 7-continued

|  | added amount (mol %) | solvent (mL) | reaction temp. (° C.) | reaction time (hr.) | yield of carboxylic acid ester (%) |
|---|---|---|---|---|---|
| Example 54 | 0.25 | — | 25 | 24 | 95 |
| Example 55 | 0.25 | — | 25 | 24 | 98 |
| Example 57 | 0.25 | — | 25 | 24 | 98 |
| Example 57 | 0.25 | — | 25 | 24 | 77 |
| Example 58 | 0.25 | THF (80) | 25 | 24 | 88 |
| Example 59 | 0.25 | THF (80) | 50 | 4 | 94 |
| Example 60 | 0.5 | — | 25 | 24 | 96 |
| Example 61 | 1.0 | — | 25 | 6 | 90 |
| Example 62 | 1.0 | — | 25 | 6 | 94 |

INDUSTRIAL APPLICABILITY

The method for producing a carboxylic acid ester related to the present invention is capable of producing the carboxylic acid ester more efficiently and cost-effectively than in conventional methods. In addition, by using the method for producing a carboxylic acid ester related to the present invention, a carboxylic acid ester is obtained at high yield under mild reaction conditions. Furthermore, since various carboxylic acids and alcohols may be used as raw materials in the method for producing a carboxylic acid ester related to the present invention, the substrate generality is significantly broader than in conventional methods.

The present application is based upon and claims the benefit of Japanese Patent Application No. 2014-255665, filed on Dec. 18, 2014. The entire contents of the application are incorporated herein by reference.

So far, the present invention has been described with reference to the embodiments and examples. However, the present invention is not limited to those embodiments and examples. Unless deviating from the gist of the present invention, various modifications to the structure and details of the present invention may be made within the scope that will be apparent to those skilled in the art.

What is claimed is:
1. A method, comprising:
reacting a compound represented by formula (I):

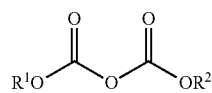

where $R^1$ and $R^2$ each independently are a C1-C20 hydrocarbon group with a carboxylic acid and an alcohol in the presence of at least one magnesium compound and at least one alkali metal compound to produce a carboxylic acid ester from said carboxylic acid and said alcohol.

2. The method according to claim 1, wherein the alkali metal compound comprises lithium.

3. The method according to claim 1, wherein the compound represented by the formula (I) is di-t-butyl dicarbonate.

4. The method according to claim 1, wherein the carboxylic acid is a (meth)acrylic acid.

5. The method according to claim 1, wherein the alcohol is an aromatic alcohol.

6. The method according to claim 1, wherein said reacting is carried out by adding 0.1-10 mol of the carboxylic acid and 0.1-10 mol of the alcohol relative to 1 mol of the compound represented by the formula (I).

7. The method according to claim 1, wherein said reacting is carried out in the presence of the magnesium compound and alkali metal compound, each being set at 0.001-1000 mol % of the alcohol.

8. The method according to claim 1, wherein said carboxylic acid is a compound represented by the formula $R^3$—COOH where $R^3$ is a C1-C30 hydrocarbon group that may have a substituent, said alcohol is a compound represented by the formula $R^4$—OH where $R^4$ is a C1-C30 hydrocarbon group that may have a substituent, and said carboxylic acid ester is a compound represented by the formula $R^3COOR^4$ where $R^3$ and $R^4$ are as described for the formulae $R^3$—COOH and $R^4$—OH.

9. The method according to claim 1, wherein the compound represented by the formula (I) is di-t-butyl dicarbonate, the carboxylic acid is (meth)acrylic acid, the alcohol is phenol, and the carboxylic acid ester is phenyl (meth)acrylate.

10. The method according to claim 1, wherein the at least one magnesium compound is selected from magnesium oxide, magnesium hydroxide, magnesium carbonate hydroxide, magnesium sulfate, ammonium magnesium sulfate, magnesium nitrate, magnesium chloride, magnesium bromide, magnesium acetate, magnesium benzoate, magnesium (meth)acrylate, and magnesium acetylacetonate, and the at least one alkali metal compound is selected from lithium oxide, lithium hydroxide, lithium carbonate, lithium fluoride, lithium chloride, lithium bromide, lithium acetate, lithium benzoate, lithium (meth)acrylate, lithium amide, lithium triflimide, and lithium acetylacetonate.

11. The method according to claim 10, wherein said carboxylic acid is a compound represented by the formula $R^3$—COOH where $R^3$ is a C1-C30 hydrocarbon group that may have a substituent, said alcohol is a compound represented by the formula $R^4$—OH where $R^4$ is a C1-C30 hydrocarbon group that may have a substituent, and said carboxylic acid ester is a compound represented by the formula $R^3COOR^4$ where $R^3$ and $R^4$ are as described for the formulae $R^3$—COOH and $R^4$—OH.

12. The method according to claim 10, wherein the compound represented by the formula (I) is di-t-butyl dicarbonate, the carboxylic acid is (meth)acrylic acid, the alcohol is phenol, and the carboxylic acid ester is phenyl (meth)acrylate.

13. The method according to claim 1,
wherein the compound represented by the formula (I) is di-t-butyl dicarbonate, the carboxylic acid is a (meth)acrylic acid, the alcohol is phenol, and the carboxylic acid ester is phenyl (meth)acrylate, and
wherein the at least one magnesium compound is selected from magnesium acetylacetonate, and the at least one alkali metal compound is selected from lithium hydroxide monohydrate, cesium hydroxide monohydrate, lithium carbonate, sodium carbonate, potassium carbonate, rubidium carbonate, cesium carbonate, lithium oxide, lithium acetylacetonate, lithium fluoride, lithium chloride, lithium bromide, lithium amide, and lithium triflimide.

* * * * *